(12) United States Patent
Haidukewych et al.

(10) Patent No.: US 8,114,079 B2
(45) Date of Patent: Feb. 14, 2012

(54) INTRAMEDULLARY NAIL WITH COUPLED SHAFTS

(75) Inventors: George J. Haidukewych, Tampa, FL (US); Anthony J. Metzinger, Winona Lake, IN (US)

(73) Assignee: DePuy Products, Inc., Warsaw, IN (US)

( * ) Notice: Subject to any disclaimer, the term of this patent is extended or adjusted under 35 U.S.C. 154(b) by 709 days.

(21) Appl. No.: 12/080,040

(22) Filed: Mar. 31, 2008

(65) Prior Publication Data
US 2009/0248025 A1    Oct. 1, 2009

(51) Int. Cl.
*A61B 17/56* (2006.01)

(52) U.S. Cl. .................. 606/67; 606/60; 606/62; 606/64

(58) Field of Classification Search .............. 606/62–68, 606/96–98, 300, 301, 305–308, 319; 411/321–323
See application file for complete search history.

(56) References Cited

U.S. PATENT DOCUMENTS

| | | | | |
|---|---|---|---|---|
| 1,017,371 | A | * | 2/1912 | Beck ............................. 411/321 |
| 2,772,676 | A | * | 12/1956 | Pohl ................................ 606/65 |
| 4,978,349 | A | * | 12/1990 | Frigg .............................. 606/67 |
| 5,019,079 | A | * | 5/1991 | Ross .............................. 606/312 |
| 5,032,125 | A | | 7/1991 | Durham et al. |
| 5,356,410 | A | | 10/1994 | Pennig |
| 5,454,813 | A | | 10/1995 | Lawes |
| 5,562,666 | A | * | 10/1996 | Brumfield ....................... 606/64 |
| 5,713,902 | A | | 2/1998 | Friedl |
| 6,228,086 | B1 | | 5/2001 | Wahl et al. |
| 6,235,031 | B1 | | 5/2001 | Hodgeman et al. |
| 6,406,477 | B1 | * | 6/2002 | Fujiwara ......................... 606/67 |
| 6,443,954 | B1 | | 9/2002 | Bramlet et al. |
| 7,442,209 | B2 | * | 10/2008 | Michelson ................. 623/17.11 |
| 2003/0004514 | A1 | | 1/2003 | Frigg et al. |
| 2005/0055024 | A1 | * | 3/2005 | James et al. ..................... 606/64 |
| 2005/0071008 | A1 | * | 3/2005 | Kirschman ................ 623/17.11 |
| 2005/0149025 | A1 | | 7/2005 | Ferrante et al. |
| 2006/0106386 | A1 | * | 5/2006 | Reber et al. ...................... 606/65 |
| 2007/0049938 | A1 | * | 3/2007 | Wallace et al. .................. 606/62 |
| 2008/0051790 | A1 | * | 2/2008 | Defossez ........................ 606/64 |
| 2008/0262498 | A1 | * | 10/2008 | Fernandez Dell'Oca ....... 606/65 |

FOREIGN PATENT DOCUMENTS

| | | |
|---|---|---|
| DE | 20320867 | 3/2005 |
| EP | 0968685 A2 | 1/2000 |
| EP | 1839608 | 10/2007 |
| WO | 8604798 | 8/1986 |

OTHER PUBLICATIONS

PCT Search Report in corresponding application (PCT/US2009/038762), mailed Aug. 6, 2009, 6 pages.

* cited by examiner

*Primary Examiner* — Eduardo C Robert
*Assistant Examiner* — Paul J Spatafore
(74) *Attorney, Agent, or Firm* — Maginot, Moore & Beck

(57) ABSTRACT

A nail assembly for use in trauma surgery is provided. The nail assembly includes an intramedullary shaft including a first transverse passage and a second transverse passage in the shaft. The first transverse passage and the second transverse passage do not contact each other on the shaft. The nail assembly also includes a first shaft extending through the first transverse passage in the intramedullary shaft and a second shaft extending through the second transverse passage in the intramedullary shaft. The second shaft includes an engagement feature configured to bring the second shaft into contact with the first shaft. The engagement feature may be in the form of a lateral mechanical feature that provides simultaneous unilateral coupled motion of the first shaft with the second shaft through the transverse passages in the intramedullary shaft.

13 Claims, 8 Drawing Sheets

INTRAMEDULLARY NAIL WITH COUPLED SHAFTS

TECHNICAL FIELD

The present invention relates generally to the field of orthopaedic trauma, and more particularly to a device for positioning in the medullary canal of a long bone.

BACKGROUND

The skeletal system includes many long bones that extend from the human torso. These long bones include the femur, fibula, tibia, humerus, radius and ulna. These long bones are particularly exposed to trauma from accidents, and, as such, may be fractured during a trauma.

Often the distal end or proximal portions of the long bone, for example the femur and the tibia, are fractured into several components and must be realigned. Mechanical devices, commonly in the forms of pins, plates, screws, nails, wires and external devices are commonly used to attach fractured long bones. The pins, plates, wires, nails and screws are typically made of a durable material compatible to the human body, for example titanium, stainless steel or cobalt chromium.

Subtrochanteric and femoral shaft fractures have been treated with the help of intramedullary rods or nails, which are inserted into the marrow canal of the femur to immobilize the femur parts involved in fractures. Subtrochanteric and femoral shaft fractures of femurs are often accompanied by fractures of the femoral neck and head. Areas around the greater trochanter and lesser trochanter may also fracture. Intramedullary rods or nails are often provided with openings for receiving transverse screws which are used to secure the femoral bone fragments, for example the greater trochanter, the lesser trochanter, the neck, and the head.

When securing bone fragments of the neck and head of the femur, a transverse screw, for example in the form of a lag screw, is fitted through an opening in the intramedullary nail and is screwed into the neck and head of the fractured femur. A solitary screw may permit the bone fragments of the neck and head of the femur to rotate about the screw and, thus, not be properly secured. Maintaining the position of the fragments of the fractures of proximal femoral fractures and trochanteric fractures is important for obtaining good reduction to promote healing. It is important that the bone fragments stay in close proximity to each other or to be in reduction to promote the healing. To assist in proper reduction of the neck and head of a femur, a second screw in the form of, for example, an anti-rotation peg or screw is positioned in a second opening in the intramedullary nail to provide a more rigid construction for securing the fractured bone fragments of the femoral neck and head.

To promote the healing of bone fractures and according to Wolfe's Law the healing of bone fragments is promoted by providing some load or force upon the reduction or fracture site. Such loading of the fracture site promotes healing. Therefore intramedullary nails have been designed to provide for sliding compression or movement of the screws in the openings of the intramedullary nail. Such threading movement of the screw in bone is undesirable. Further, when utilizing a lag screw and an anti-rotation screw in an intramedullary nail, a phenomenon known as the "z effect" may occur. The z-effect occurs when the lag screw or the anti-rotation screw moves in a first direction and the other of the lag screw and the other rotation screw moves in the opposing direction. With the z-effect one screw moves toward the lateral femoral shaft wall while the other screw moves toward the femoral head. Further, while it may be desirable to provide for sliding compression in an intramedullary nail to promote healing, desires to avoid the z-effect and other patient indications may make the use of a locked nail assembly preferred. In a locked nail assembly the transverse screws are rigidly secured to the nail. Therefore, it would be advantageous to provide an improved intramedullary nail assembly.

SUMMARY

According to one embodiment of the present disclosure, there is provided a nail assembly for use in trauma surgery. The nail assembly includes an intramedullary shaft including a first transverse passage and a second transverse passage in the shaft. The first transverse passage and the second transverse passage do not contact each other on the shaft. The nail assembly also includes a first shaft extending through the first transverse passage in the intramedullary shaft and a second shaft extending through the second transverse passage in the intramedullary shaft. The second shaft includes an engagement feature configured to bring the second shaft into contact with the first shaft. The engagement feature may be in the form of a lateral mechanical feature that provides simultaneous unilateral coupled motion of the first shaft with the second shaft through the transverse passages in the intramedullary shaft.

According to another embodiment of the present disclosure there is provided a nail assembly for use in trauma surgery. The nail assembly includes an intramedullary shaft defining first and second openings in the shaft. The first shaft is fitted to the first opening in the intramedullary shaft and defines a coupling feature of the first shaft. The second shaft is fitted to the second opening. The second shaft includes an enlarged portion on one end of the shaft with a coupling feature provided on the enlarged portion. The first shaft is separated from the second shaft within the intramedullary shaft. The coupling feature of the first shaft and the coupling feature of the second shaft cooperate with each other to limit the movement of the first shaft relative to the second shaft.

According to yet another embodiment of the present disclosure there is provided a method for performing trauma surgery on a long bone. The method includes the step of inserting an intramedullary nail into the medullary canal of the long bone. The intramedullary nail has first and second openings extending from an insertion side to a removal side of the intramedullary nail. The method also includes the steps of inserting a first end of a lag screw into the first opening of the intramedullary nail from the insertion side of the intramedullary shaft and inserting a first end of a bone screw into the second opening of the intramedullary nail from the insertion side of the intramedullary shaft. The method also includes the steps of coupling the lag screw to the bone screw, after inserting the first end of the bone screw into the second opening of the intramedullary shaft.

Technical advantages of the present invention will be readily apparent to one skilled in the art from the following figures, descriptions and claims.

BRIEF DESCRIPTION OF THE DRAWINGS

Corresponding reference characters indicate corresponding parts throughout the several views. Like reference characters tend to indicate like parts throughout the several views.

DETAILED DESCRIPTION OF THE INVENTION

Figure 1:
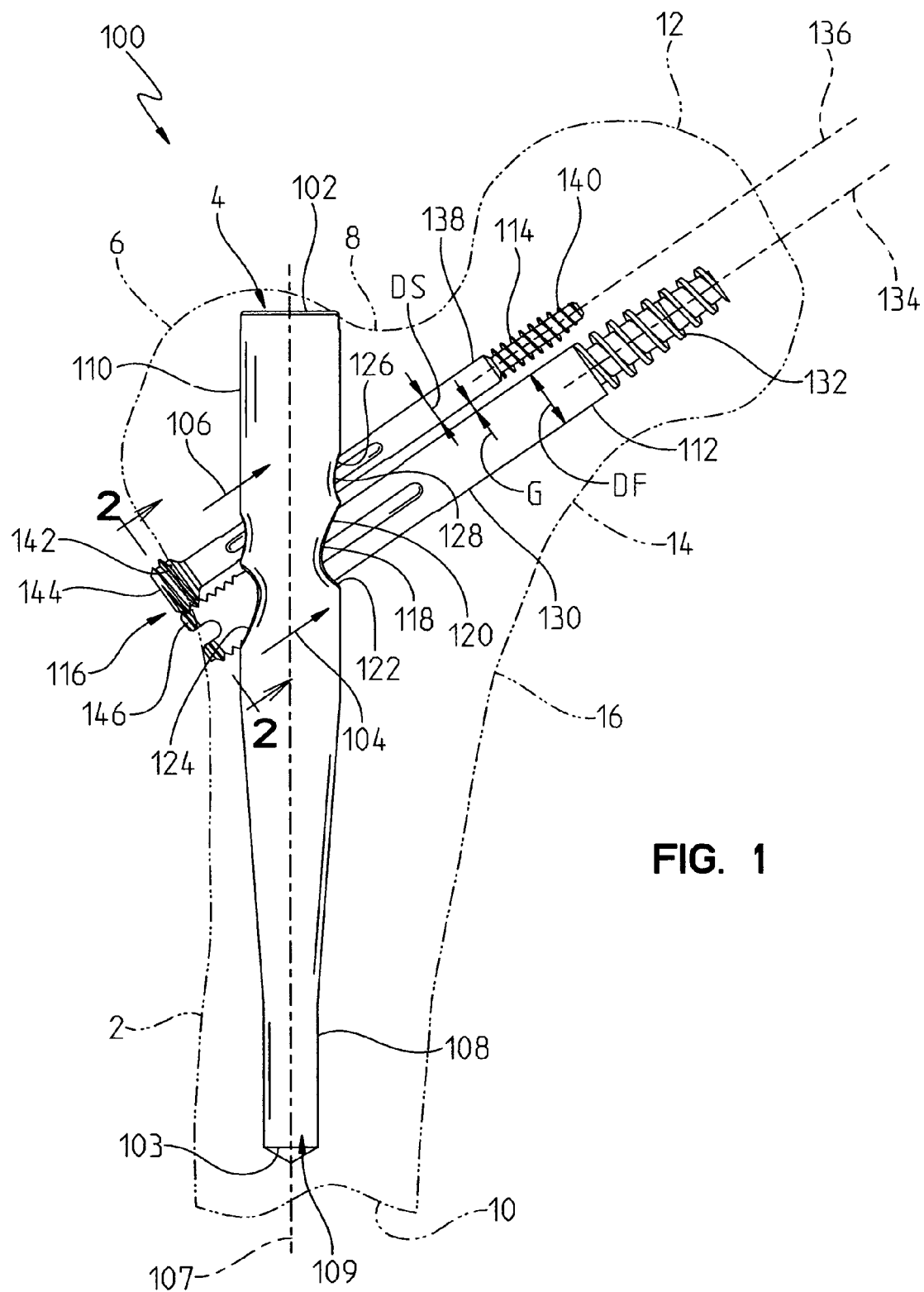
FIG. 1 is an anterior posterior view of an intramedullary nail assembly in accordance with an embodiment of the present disclosure including a nail and coupled transverse screws.

According to the present disclosure and referring now to FIG. 1 a nail assembly 100 for use in trauma surgery is shown. The nail assembly 100 may be utilized in any suitable long bone, for example femur 2. Alternatively, the nail assembly 100 may be used on a tibia, fibula, ulna, radius, or humerus. The nail assembly 100 may be particularly well suited for use in the humerus which contains a head and has a shape somewhat similar to that of a femur 2.

The nail assembly 100 includes an intramedullary shaft 102 having a first transverse passage 104 and a second transverse passage 106 in the intramedullary shaft 102. The first transverse passage 104 and the second transverse passage 106 are not in contact with each other.

The shaft 2 may have any suitable shape such that the intramedullary shaft 102 may be fitted into a long bone, for example into the medullary canal 4 of the femur 2. Since the medullary canal 4 is generally cylindrical, the intramedullary shaft 102 typically has a generally cylindrical shape. The intramedullary shaft 102 may include a distal portion 108 having a smaller size or diameter than proximal portion 110 of the intramedullary shaft 102. The intramedullary shaft 102 may be inserted through greater trochanter 6 of the femur 2. Alternatively, the intramedullary shaft 102 may be inserted through piriformis fossa 8 or be in the form of a retrograde nail and may be inserted through distal end 10 of the femur 2.

The shaft 102 typically has a length greater than its width or diameter and may extend partially or substantially the entire length of the intramedullary canal 4 of the femur 2. The intramedullary shaft 102 may be straight or may be arcuate along longitudinal axis 107 of the intramedullary shaft 102 to conform to the natural arc of the femur 2. The shaft 102 may include a longitudinal opening 109 or a longitudinal slot (not shown) to reduce pressure while inserting the intramedullary shaft 102 into the canal 4.

The nail assembly 100 of FIG. 1 further includes a first shaft 112 extending through the first transverse passage 104 in the intramedullary shaft 102. The nail assembly 100 further includes a second shaft 114 extending through the second transverse passage 106 in the intramedullary shaft 102. The second shaft 114 includes an engagement feature 116 configured to bring the second shaft 114 into contact with the first shaft 112.

The first transverse passage 104 in the intramedullary shaft 102 may, as is shown in FIG. 1, be formed by first internal wall 118 in the intramedullary shaft 102. The first internal wall 118 forms a periphery 120 of the first internal wall 118. The longitudinal opening 109 of the shaft 102 separates first internal wall 118 into a medial portion 122 and a lateral portion 124. Similarly, the second transverse passage 106 may be formed in intramedullary shaft 102 by a second internal wall 126 formed in the intramedullary shaft 102. The second internal wall 126 defines a periphery 128 of the second internal wall 126. Similarly, the second internal wall 126 may have medial and lateral portions.

The first shaft 112 may be fitted in any manner to the first transverse passage 104. To permit sliding compression of the first shaft 102 with respect to the intramedullary shaft 102, the first shaft 112 may be slidably fitted to the first transverse passage 104. Similarly, the second shaft 114 may be slidably fitted to the second transverse passage 106 of the intramedullary shaft 102.

It should be appreciated that the transverse passages 104 and 106 may be oriented in any direction such that any portion of the bone desired to be reduced may be captured by the screw fitted to the opening. For example, the femur 2 may include a head 12 extending from neck 14 of the femur 2. The femur 2 may further include a lesser trochanter 16 in addition to greater trochanter 6. It should be appreciated that the transverse passages 104 and 106 may be oriented to be in alignment with the greater trochanter 6 and the lesser trochanter 16 or, as shown in FIG. 1, the first transverse passage 106 and the second transverse passage 106 may be oriented such that the first shaft 112 and the second shaft 114 extend into the neck 14 and the head 12 of the femur 2.

The first shaft 112 may have any suitable size and shape such that the first shaft 112 is utilized to assist in reducing a fracture of the long bone 2. For example and as shown in FIG. 1, the first shaft 112 is in the form of a bone screw. For example and as shown in FIG. 1, the bone screw 112 is in the form of a lag screw. The lag screw 112 includes a generally cylindrical stem 130 with diameter DF and distal threads 132 extending from an end of the stem 130. The lag screw 112 may be cannulated.

The lag screw 112 as shown in FIG. 1 may be rigidly secured in the first transverse passage 104 of shaft 102 or may slide within first transverse passage 104 along longitudinal axis 134 of the first passage 104. The second shaft 114, as shown in FIG. 1, is spaced from first shaft 112 a distance G. The distance G is preferably sufficient to provide stability for the head 12 of the femur 2 when the first shaft 12 and the second shaft 14 are engaged with a fractured head 12 so that the head 12 remains in a reduced state against neck 14 of the femur 2.

The second shaft 114 may have any suitable size and shape and preferably has a diameter DS of the second shaft 114 that slidably moves along longitudinal axis 136 of the second transverse passage 106. The sliding movement of the second shaft 114 within the second transverse passage 106 and of the first shaft 112 within the first transverse passage 104 provides for sliding compression of the fracture and promotes the healing process. The second shaft 106 includes the engagement feature 116 which is configured to bring the second shaft 114 into contact with the first shaft 112.

Since the second shaft 114 serves primarily to provide stability to the fractured head 12, the second shaft may be a pin. Alternatively and as shown in FIG. 1, the second shaft 114 may be in the form of a bone screw including a stem 138 as well as threads 140 extending from a first end of the stem 138.

The engagement feature 116 of the second shaft 114 may have any suitable configuration to provide for contact with the first shaft 112. It should be appreciated that the contact may be minimal. Alternatively, and as shown in FIG. 1, the contact between the first shaft 112 and the second shaft 114 may form a coupling between the first shaft 112 and the second shaft 114. The coupling may provide a limit to the relative motion of the first shaft 112 with respect to the second shaft 114 in some direction. For example and as shown in FIG. 1, the engagement feature 116 may be adapted to limit the rotation of the first shaft 112 with respect to the second shaft 114 along the longitudinal axes of the shafts 112 and 114. For example and as shown in FIG. 1, the engagement feature 116 is in the form of external threads 142 formed on head 144 of the second shaft 114. Alternatively the engagement feature 116 may limit the rotation of the second shaft 114 with respect to the first shaft 112.

Figure 2:
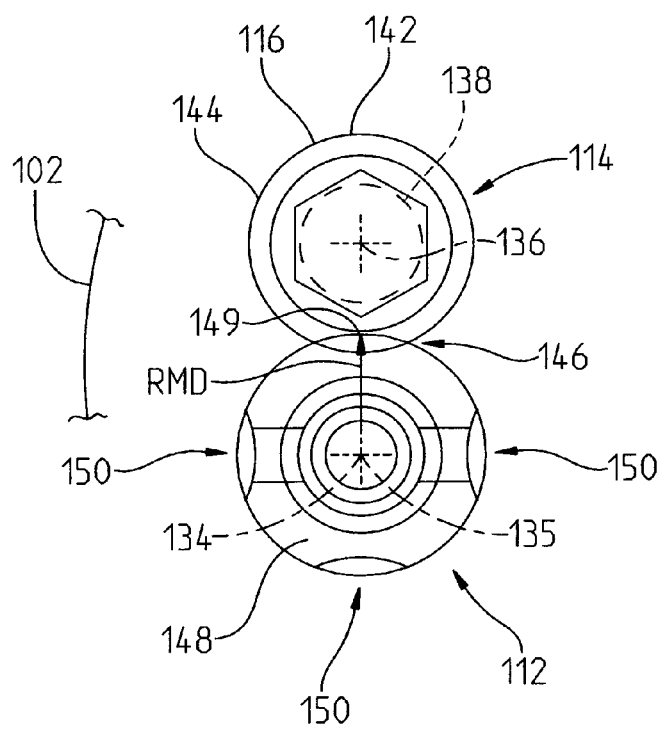
FIG. 2 is a partial cross section view of FIG. 1 along the line 2-2 in the direction of the arrows.

Referring now to FIG. 2 the engagement feature 116 of the second shaft 114 includes the external threads 142 which extend the full circumference of the second shaft 114. The first shaft 112 includes a first external threaded portion 146 located on second end 148 of stem 130 that mates with the external threads 142 of the second shaft 114. While the external threads 142 of the second shaft 114 extend the full circumference of the second shaft 114, the first threaded portion 146 of the first shaft 112 extends only a portion of the circumference of the first shaft 112. The external threads 142 of the second shaft 114 serve as a lateral mechanical feature of the second shaft 114 that cooperates with first external threaded portion 146 of the first shaft 112. The external threaded portion 146 of the first shaft 112 serves as a lateral mechanical feature of the first shaft 114. The lateral mechanical feature of the first shaft 114 is coupled to the lateral mechanical feature of the second shaft 114 to provide simultaneous unidirectional coupled motion of the first shaft 112 to the second shaft 114. As shown in FIG. 2, the first external threaded portion 146 is only located in that portion of first shaft 112 that is in engagement with the threads 142 of the second shaft 114. Therefore as can be seen in FIG. 2, since the longitudinal axis 134 of the first passage 104 is in a fixed position with respect to the longitudinal axis 136 of the second passage 106, the first shaft 112 is unable to rotate about longitudinal axis 134 of the first passage 104. Therefore, the engagement feature 116 serves to prohibit the rotation of the first shaft 112 about longitudinal axis 134 of the first passage 104.

Figure 3:
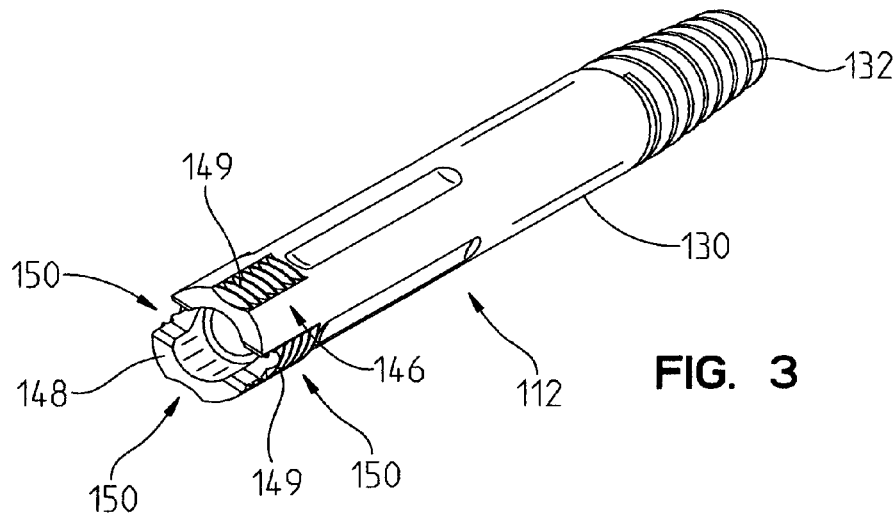
FIG. 3 is a partial perspective view of a transverse screw of the nail assembly of FIG. 1 having external threads on a portion of its periphery.

While the first external thread portion 146 may be sufficient for the first shaft 112 of the nail assembly 100, as shown in FIGS. 2 and 3 the first shaft 112 may further include additional threaded portions 150 positioned in spaced-about locations from the first external threaded portion 146 of the first shaft 112. The additional threaded portions 150 permit the shaft 112 to be rotated a portion of a revolution prior to the insertion of the second shaft 114. The first shaft 112 further includes a longitudinally extending blocking structure interposed between the first external thread portion 146 and each adjacent additional threaded portion 150, as shown in FIGS. 2 and 3. It should be appreciated that the second shaft 114 may be assembled on the intramedullary shaft 102 after the first shaft 112 is assembled onto the intramedullary shaft 102. Once assembled, the first shaft 112 may be rotated a portion of a revolution such that the first threaded portion 146 or one of the additional threaded portions 150 is in alignment with the threads 142 of the second shaft 114.

The first threaded portion 146 and the additional threaded portions 150 of the first shaft 112 define crests 149 of the teeth of the threaded portions 146 and 150 that defines a convex surface. For example, and as shown in FIG. 2 the crests 149 are defined by a radius RMD extending from longitudinal axis 135 of the first shaft 112. The threaded portions 146 and 150 of the first shaft 112 may have any suitable shape and may have crests that, for example, are linear or straight or, alternatively may have crests that are concave.

Referring again to FIG. 1, the nail assembly 100 is assembled by first inserting the distal end 103 of the nail 102 through the greater trochanter 6 of femur 2 and then into the intramedullary canal 4 of the femur 2. The nail 102 is advanced into the canal 4 until the proximate portion 110 of the nail 102 is received within the greater trochanter 6 of the femur 2. The lag screw 112 is then inserted into the lateral side 124 and then into the medial side 122 of the first transverse passage 104 formed in the nail 102. Then the lag screw 112 is threaded into position until the threaded portion 132 of the lag screw 112 reduces the head 12 of the femur 2 against the neck 14 of the femur 2. The lag screw 112 is then rotated, as shown in FIG. 2, until one of the threads 146 and 150 of the lag screw 112 is pointing upwardly such that it is in alignment for the insertion of the anti-rotation screw 114.

Next the anti-rotation screw 114 is inserted with the threads 140 of the anti-rotation screw 114 first inserted into the second transverse passage 106 of nail 102. The anti-rotation screw 114 is inserted first into the lateral side and then into the medial side of the second transverse passage 106 of the nail 102. The anti-rotation screw 114 is advanced until the threads 140 of the anti-rotation screw 114 engage the head 12 of the femur and assist in reducing the head 12 against the neck 14 of the femur 2. The engagement feature 116 in the form of internal threads 142 formed on head 144 of anti-rotation screw 114 are then threaded into engagement with the external threaded portions 146 or 150 of the lag screw 112, locking the lag screw 112 to the anti-rotation screw 114.

Figure 2A:
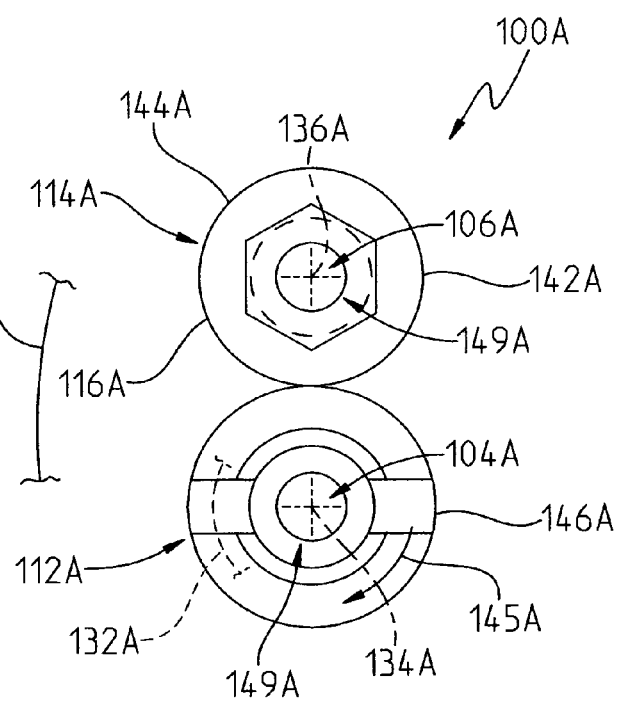
FIG. 2A is a partial cross section view of an alternate embodiment of the present disclosure with an alternate configuration for the coupling of the transverse screws.

Referring now to FIG. 2A another embodiment of the present disclosure is shown as nail assembly 100A. The nail assembly 100A is similar to the nail assembly 100 and includes an intramedullary shaft 102A identical to shaft 102 of the nail assembly 100 of FIG. 1. The nail assembly 100A of FIG. 2A includes a first shaft 112A having external threads 146A extending the full circumference of the first shaft 112A. The threads 148A of the first shaft 112A are in engagement with threads 142A formed in head 144A of second shaft 114A. Bone threads 132A of the first shaft 112A have a lead opposite that of the threads 146A. It should be appreciated that as the first shaft 112A rotates in the direction of arrow 145A as it advances in the direction of arrow 149A, the second shaft 114A does not rotate, but advances in the direction of arrow 149A.

By configuring the threads 132A and 148A with threads in which one is left handed and the other is right handed, the rotation of the first shaft 112A in the direction of arrow 145A will cause the non-rotating second shaft 114A to advance in the direction of arrow 149A. The shafts 112A and 114A both advance laterally in the direction of arrow 149A along longitudinal axes 134A and 136A of passages 104A and 106A, respectively. Thus, engagement feature 116A of the second shaft 114A and the first shaft 112A cooperate with each other such that if one of the first shaft 112A and the second shaft 114A rotates and advance laterally along its rotational axis in the first direction the other of the first shaft 112A and the second shaft 114A will likewise advance laterally in a direction parallel to the first direction.

Figure 4:
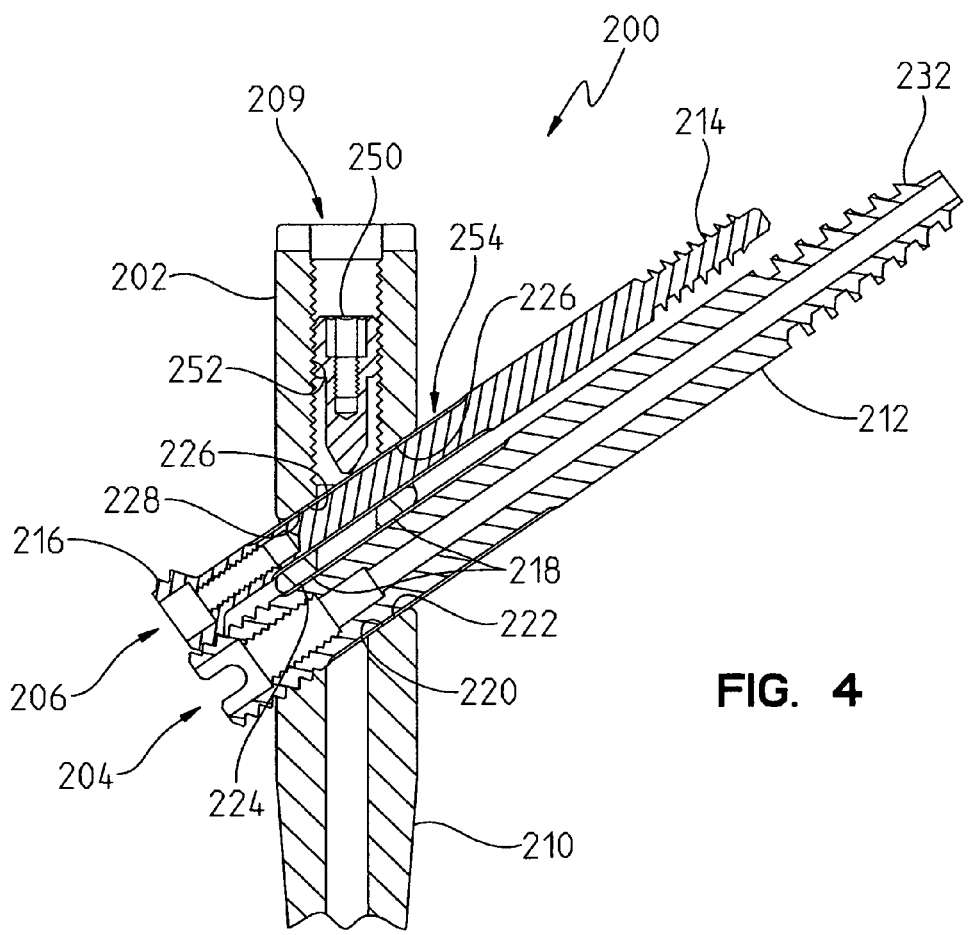
FIG. 4 is a partial cross section view of FIG. 1 showing the coupling of the transverse screws.

Referring now to FIG. 4, another embodiment of the present disclosure is shown as nail assembly 200. The nail assembly 200 is similar to the nail assembly 100 of FIGS. 1 to 3 except that the nail assembly 200 further includes a locking screw 250 headedly engaged with internal threads 252 formed in longitudinal opening 209 of intramedullary shaft 202. The locking screw 252 engages a longitudinal slot 254 formed in second shaft 214 to prevent the rotation of second shaft 214. Engagement feature 216 of the second shaft 214 prevents rotation of the first shaft 212. Thereby the locking screw 250 is effective in locking the first shaft 212 as well as the second shaft 214. The threads 232 of lag screw 212 have a truncated asymmetrical profile for easy cutting medially though the cancellous bone and to resist rotation corresponding to lateral motion of the screw 212 in the head 12 of the femur 2. This profile is more fully described in Published US Patent Application Publication No. 2007/0049938, incorporated by reference herein in its entirety.

Figure 5:
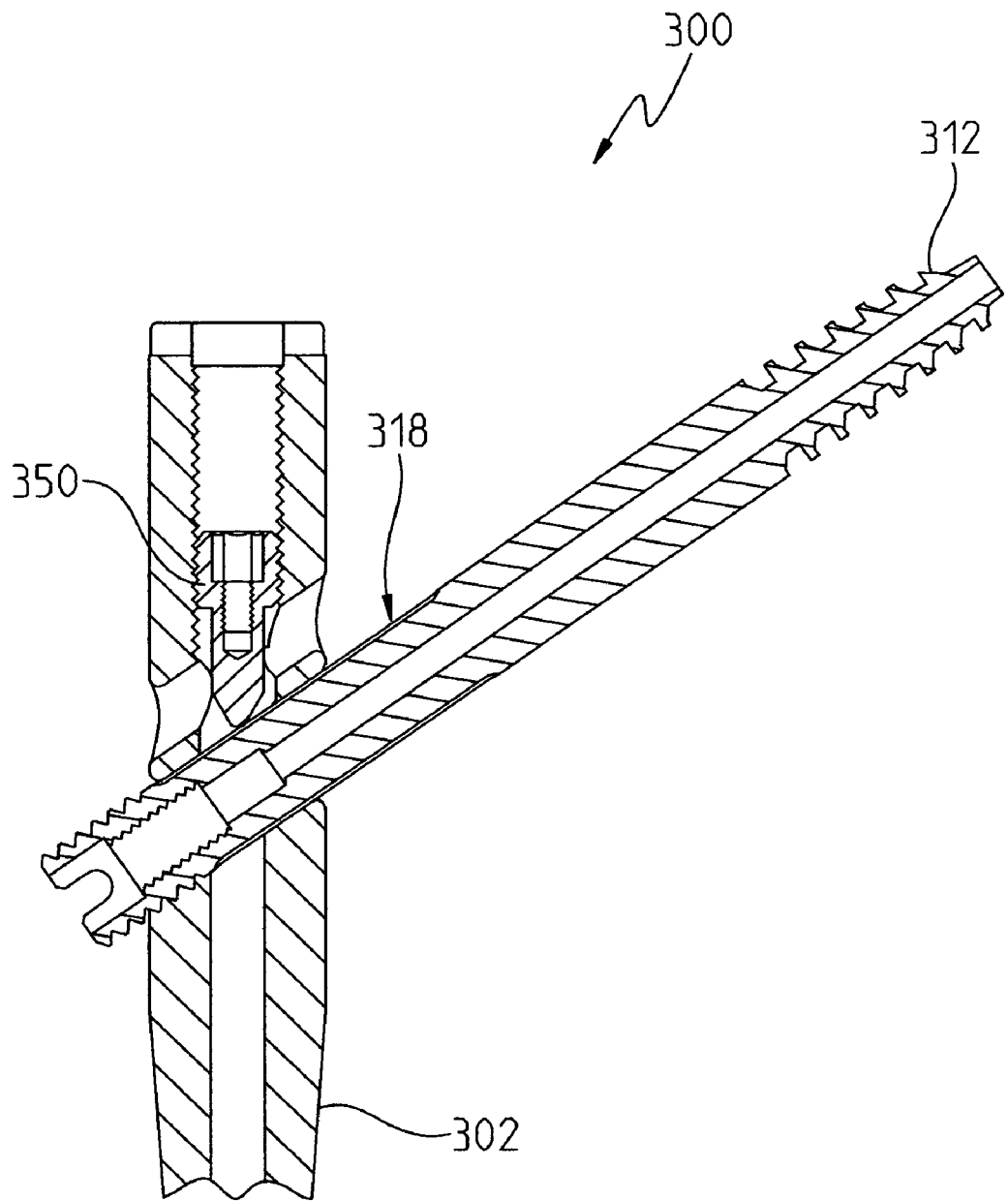
FIG. 5 is a cross sectional view of the nail of the nail assembly of FIG. 1 with the lag screw of the nail assembly of FIG. 1 assembled to the nail and without the anti-rotation screw of FIG. 1.

Referring now to FIG. 5, yet another embodiment of the present invention is shown as intramedullary nail assembly 300. The nail assembly 300 is similar to the nail assembly 200 of FIG. 4 except that the nail assembly 300 does not include the second shaft 214. A locking screw 350 engages longitudinal groove 318 of first screw 312 to lock the first screw 312 to intramedullary nail 302.

Figure 6:
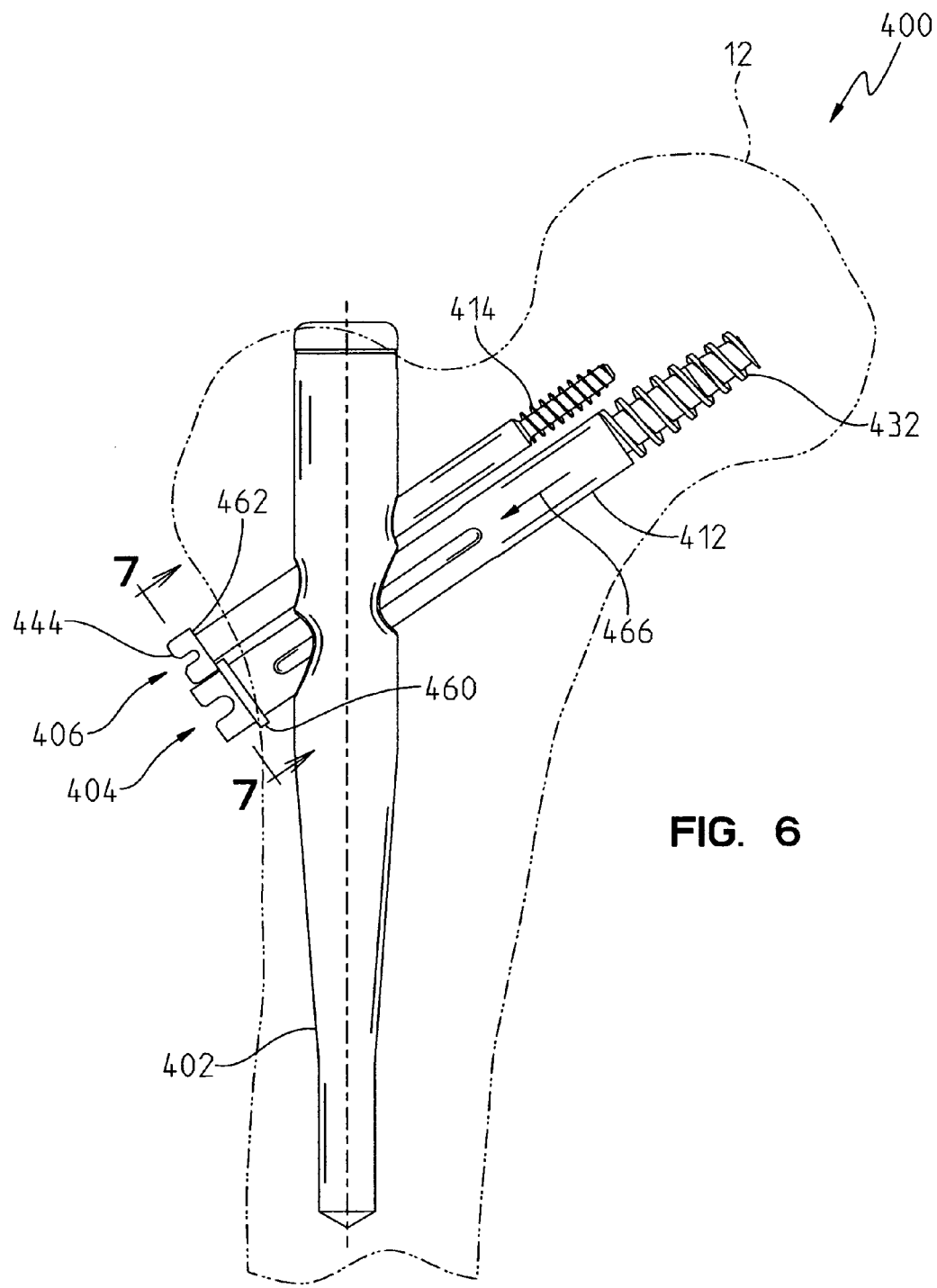
FIG. 6 is an anterior posterior view of an intramedullary nail assembly in accordance with another embodiment of the present disclosure including a nail and transverse screws coupled by a collar.
Figure 7:
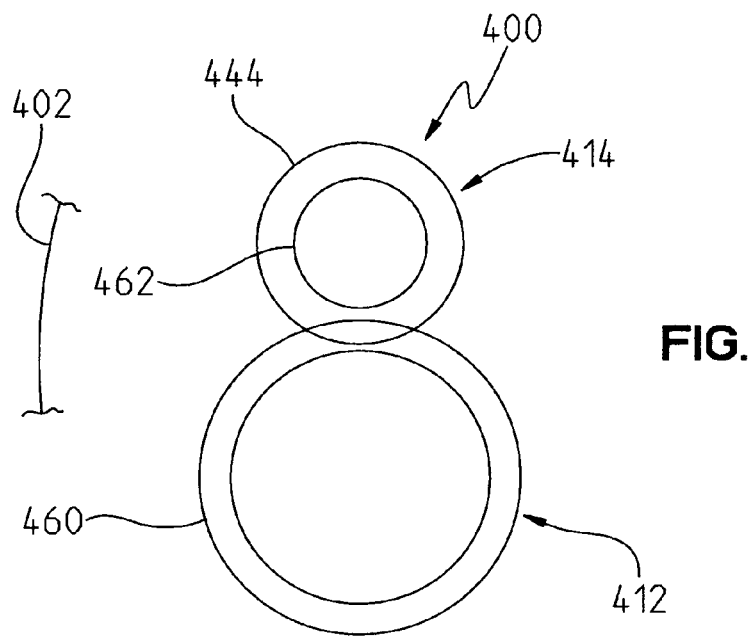
FIG. 7 is a partial cross section view of FIG. 6 along the line 7-7 in the direction of the arrows.

Referring now to FIGS. 6 and 7, another embodiment of the present invention is shown as intramedullary shaft assembly or intramedullary nail assembly 400. The nail assembly 400 is similar to the nail assembly 100 of FIGS. 1 to 3 except that the nail assembly 400 includes a different mechanism for connecting or coupling the first shaft or screw to the second shaft or screw. For example, and as shown in FIG. 6 the nail assembly 400 includes a nail 402 similar to the nail 102 of FIGS. 1 to 3. The nail assembly 400 also includes a first shaft in the form of first lag screw 412 similar to the first lag screw 112 of FIGS. 1 to 3. The nail assembly 400 also includes a second shaft or second screw, for example a second or an anti-rotation screw 414 similar to the shaft 114 of the FIGS. 1 through 3. The lag screw 412 slidably fits into first transverse passage 404 of the nail 402 and the second screw 414 slidably fits into second transverse opening 406 of the nail 402.

The first screw 412 includes a coupling feature 460 in the form of an annular ring which cooperates with a coupling feature 462 in the form of a shoulder formed by head 444 of the second screw 414. The diameter of head 444 is in touching engagement with the first lag screw 412. It should be appreciated and as shown in FIGS. 6 and 7, the first lag screw 412 and the second screw 414 may be independently rotated and are not locked to each other. It should be further appreciated that the anti-rotation screw 414 serves to limit the motion of the lag screw 412 in the lateral direction or in the direction arrow 466. The threads 432 of lag screw 412 have a thin profile for easy cutting though the cancellous bone and to preserve most of the cancellous bone for securing the head 12 to the screw 412.

Figure 7A:
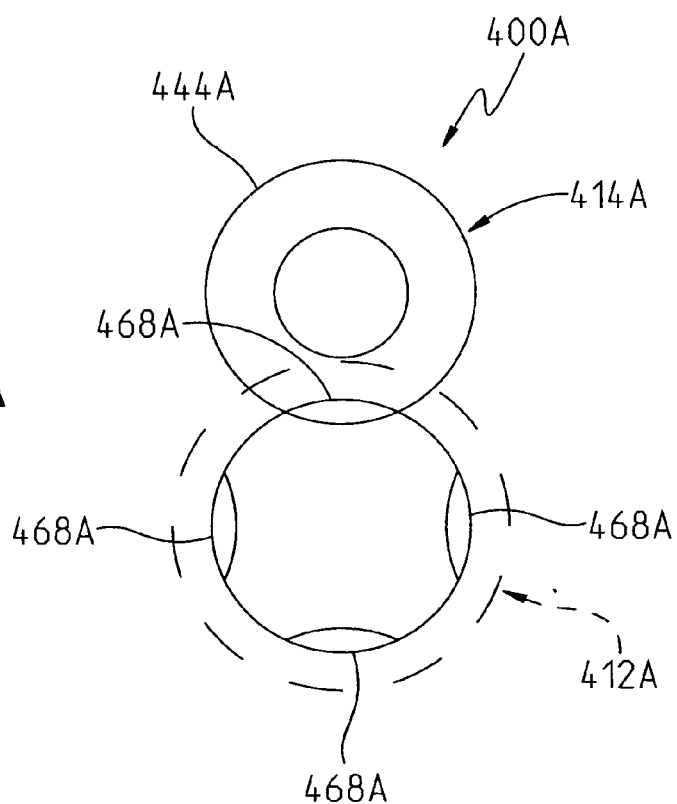
FIG. 7A is a view similar to FIG. 7, but showing an alternative embodiment of the nail assembly 400.

Referring now to FIG. 7A another embodiment of the present disclosure is shown as nail assembly 400A. The nail assembly 400A is very similar to the nail assembly 400 of FIGS. 6 and 7 except that the nail assembly 400A includes a lag screw 412A which has spaced apart recesses or scallops 468A which engage with head 444A of the second screw 414A. The grooves or scallops 468A serve to prohibit the rotation of the lag screw 412A about its longitudinal axis.

Figure 8:
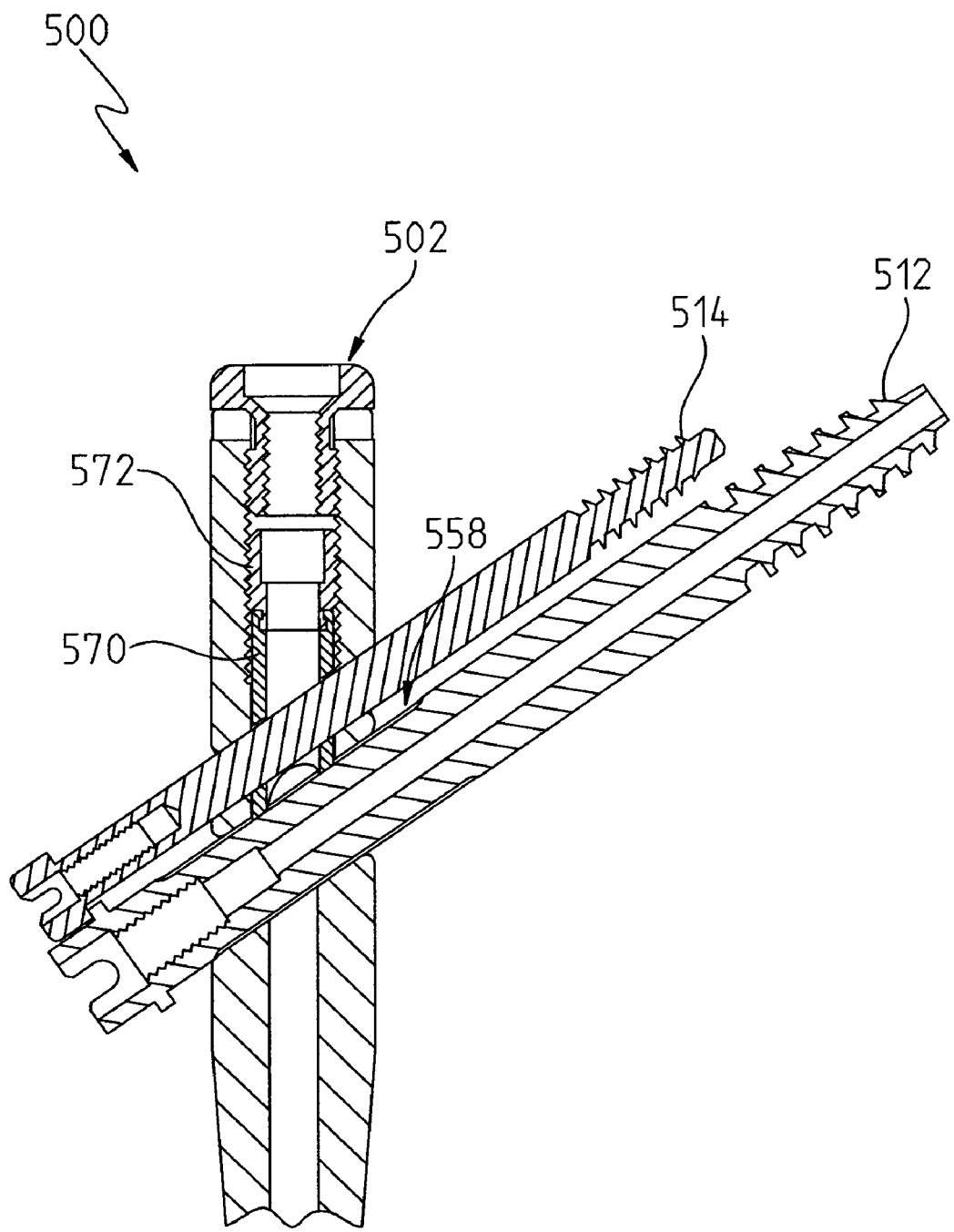
FIG. 8 is a partial cross section view of FIG. 6.

Referring now to FIG. 8 another embodiment of the present disclosure is shown as nail assembly 500. The nail assembly 500 is similar to the nail assembly 400 of FIGS. 6 and 7 except that the nail assembly 500 further includes a locking sleeve or liner 570 which is advanced by a set screw 572 to engage a longitudinal groove 558 formed in lag screw 512. The lag screw 512 is identical to the lag screw 412 of FIGS. 6 and 7 and the nail assembly 500 includes a nail 502 identical to the nail 402 of the nail assembly 400 to FIGS. 6 and 7 and includes an anti-rotation screw 514 identical to the anti-rotation screw 414 of the nail assembly 400 of FIGS. 6 and 7. The liner 570 cooperates with groove 558 in the lag screw 512 to prevent the rotation of the lag screw 512. The liner 570 and the set screw 572 provide for a locked condition of the lag screw 512 such that the nail assembly 500 does not provide for sliding compression of the lag screw 512 of the nail assembly.

Figure 9:
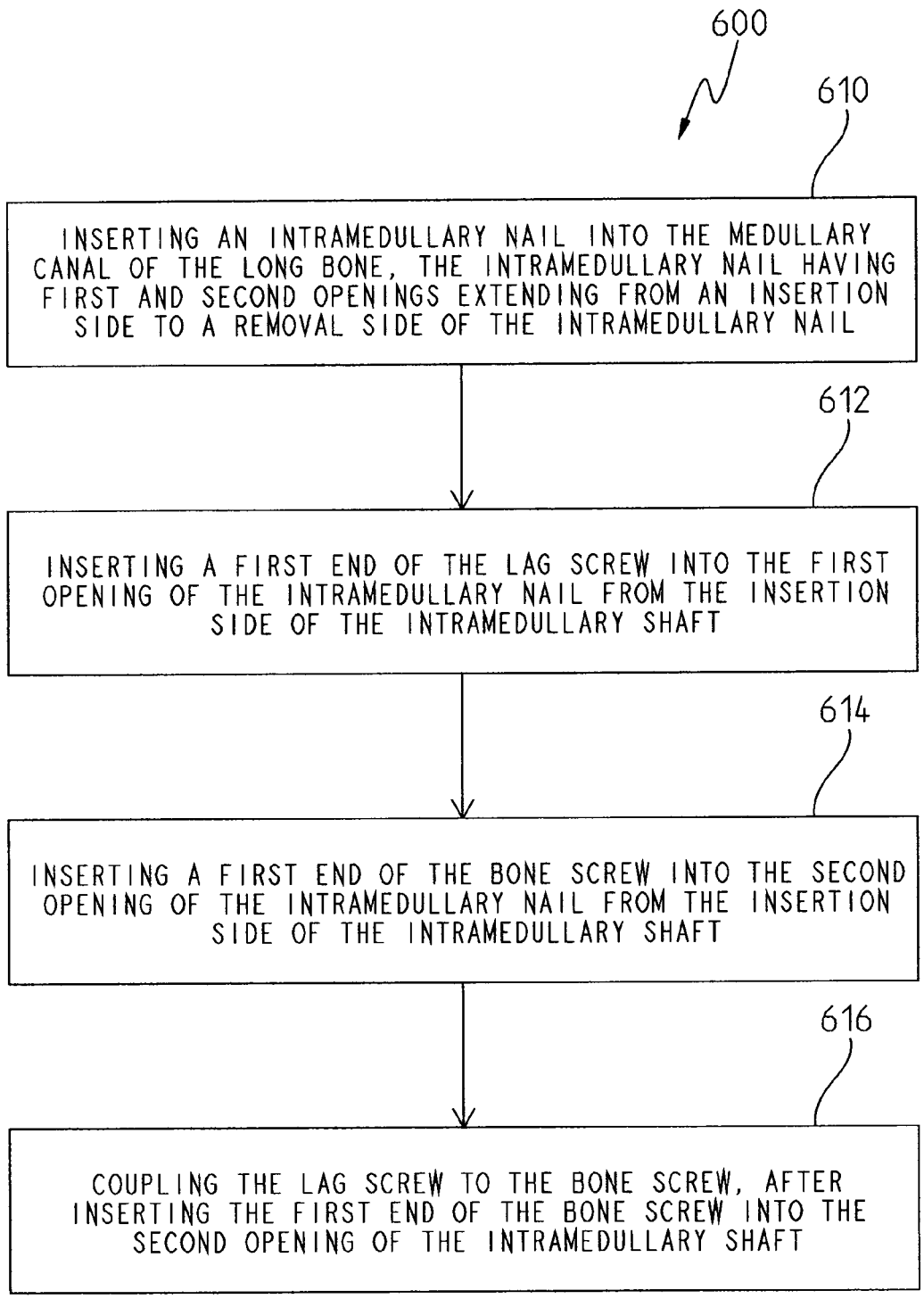
FIG. 9 is a flow diagram of a method of performing trauma surgery in accordance with another embodiment of the present disclosure.

Referring now to FIG. 9 yet another embodiment of the present disclosure is shown as surgical procedure 600. The surgical procedure 600 includes inserting an intramedullary nail into the medullary canal of the long bone, the intramedullary nail having first and second openings extending from an insertion side to a removal side of the intramedullary nail (block 610). The surgical procedure 600 further includes inserting a first end of a lag screw into the first opening of the intramedullary nail from the insertion site of the intramedullary shaft (block 612).

The surgical procedure 600 further includes inserting a first end of a bone screw into the second opening of the intramedullary nail from the insertion site of the intramedullary shaft (block 614). The surgical procedure 600 further includes coupling the lag screw to the bone screw, after inserting the first end of the bone screw into the second opening into the intramedullary shaft (block 616).

Of course, numerous other adaptations are possible. Moreover, there are advantages to individual advancements described herein that may be obtained without incorporating other aspects described above. Therefore, the spirit and scope of the appended claims should not be limited to the description of the preferred embodiments contained herein.

What is claimed is:

1. An intramedullary nail assembly, comprising:
   an intramedullary shaft including (i) a lateral sidewall portion having a first lateral orifice structure that defines a first lateral opening and a second lateral orifice structure that defines a second lateral opening, and (ii) a medial sidewall portion having a first medial orifice structure that defines a first medial opening and a second medial orifice structure that defines a second medial opening;
   a first shaft extending through said first lateral opening and said first medial opening and spaced apart from said second lateral opening and said second medial opening, said first shaft having (i) a first head portion possessing a first engagement feature, and (ii) a first stem portion defining a first shaft axis; and
   a second shaft extending through said second lateral opening and said second medial opening and spaced apart from said first lateral opening and said first medial opening, said second shaft having (i) a second head portion possessing a second engagement feature, and (ii) a second stem portion defining a second shaft axis that is substantially parallel to said first axis,
   wherein said first engagement feature contacts said second engagement feature so as to inhibit axial movement of said first shaft with respect to said second shaft, and
   wherein said first stem portion is spaced apart from said second stem portion,
   wherein said first engagement feature includes a first set of external threads, wherein said second engagement feature includes a second set of external threads, and wherein said first set of external threads are meshingly engaged with said second set of external threads.

2. The intramedullary nail assembly of claim 1, wherein:

said first set of external threads extends only partially around a circumference of said first shaft, and said second set of external threads extends completely around a circumference of said second shaft.

3. The intramedullary nail assembly of claim 2, wherein:

said first shaft includes a first longitudinally extending blocking structure and a second longitudinally extending blocking structure, said first longitudinally extending blocking structure and said second longitudinally extending blocking structure define a space therebetween, said first set of external threads is positioned in said space.

4. The intramedullary nail assembly of claim 3, wherein said second set of external threads is also positioned in said space when said first engagement feature is positioned in contact with said second engagement feature.

5. The intramedullary nail assembly of claim 1, further comprising an externally threaded set screw having a contact end portion, wherein:

said intramedullary shaft includes an internally threaded portion that defines a central passageway configured to receive said externally threaded set screw, said first shaft includes a first longitudinally extending groove defined in a first exterior surface thereof, and said contact end portion of said externally threaded set screw is configured to be received into said first longitudinally extending groove so as to inhibit rotational movement of said first shaft with respect to said intramedullary shaft.

6. The intramedullary nail assembly of claim 5, wherein:

said second shaft includes a second longitudinally extending groove defined in a second exterior surface thereof, and said contact end portion of said externally threaded set screw is configured to be received into said second longitudinally extending groove so as to inhibit rotational movement of said second shaft with respect to said intramedullary shaft.

7. The intramedullary nail assembly of claim 1, wherein said first lateral orifice structure and said second lateral orifice structure are spaced apart from each other.

8. The intramedullary nail assembly of claim 7, wherein said lateral sidewall portion includes a lateral wall segment that is interposed between said first lateral orifice structure and said second lateral orifice structure.

9. The intramedullary nail assembly of claim 7, wherein said first medial orifice structure and said second medial orifice structure are spaced apart from each other.

10. The intramedullary nail assembly of claim 8, wherein:

said first medial orifice structure and said second medial orifice structure are spaced apart from each other, said lateral sidewall portion includes a lateral wall segment that is interposed between said first lateral orifice structure and said second lateral orifice structure, and said medial sidewall portion includes a medial wall segment that is interposed between said first medial orifice structure and said second medial orifice structure.

11. The intramedullary nail assembly of claim 1, wherein:

said first stem portion includes a first externally threaded distal portion configured to be received in bone, said second stem portion includes a second externally threaded distal portion configured to be received in bone, and said first externally threaded distal portion is spaced apart from said second externally threaded distal portion.

12. The intramedullary nail assembly of claim 1, wherein:

said first shaft is an anti-rotation screw, and said second shaft is a lag screw.

13. The intramedullary nail assembly of claim 12, wherein said intramedullary shaft is an intramedullary nail.

* * * * *

UNITED STATES PATENT AND TRADEMARK OFFICE
CERTIFICATE OF CORRECTION

PATENT NO. : 8,114,079 B2
APPLICATION NO. : 12/080040
DATED : February 14, 2012
INVENTOR(S) : George J. Haidukewych et al.

It is certified that error appears in the above-identified patent and that said Letters Patent is hereby corrected as shown below:

Column 3,
Line 8, replace "screws." with --screws;--

Column 4,
Line 21, replace "first shaft 102" with --first shaft 112--

Column 7,
Line 16, replace "though" with --through--

Column 7,
Line 55, replace "though" with --through--

Signed and Sealed this
Fifth Day of March, 2013

Teresa Stanek Rea
*Acting Director of the United States Patent and Trademark Office*